US011033672B2

(12) United States Patent
Turner

(10) Patent No.: US 11,033,672 B2
(45) Date of Patent: Jun. 15, 2021

(54) CONTROL SYSTEM

(71) Applicant: Spectrum Medical Limited, Gloucester (GB)

(72) Inventor: Stephen Turner, Gloucester (GB)

(73) Assignee: Spectrum Medical Ltd., Gloucester (GB)

(*) Notice: Subject to any disclaimer, the term of this patent is extended or adjusted under 35 U.S.C. 154(b) by 474 days.

(21) Appl. No.: 15/760,346

(22) PCT Filed: Sep. 6, 2016

(86) PCT No.: PCT/GB2016/052740
§ 371 (c)(1),
(2) Date: Mar. 15, 2018

(87) PCT Pub. No.: WO2017/046567
PCT Pub. Date: Mar. 23, 2017

(65) Prior Publication Data
US 2018/0250464 A1    Sep. 6, 2018

(30) Foreign Application Priority Data
Sep. 16, 2015    (GB) .................................... 1516395

(51) Int. Cl.
*A61M 1/10*    (2006.01)
*A61M 1/36*    (2006.01)
(Continued)

(52) U.S. Cl.
CPC ........ *A61M 1/3663* (2013.01); *A61M 1/3621* (2013.01); *A61M 1/3664* (2013.01);
(Continued)

(58) Field of Classification Search
CPC .............. A61M 1/1006; A61M 1/1086; A61M 1/3621; A61M 1/3663; A61M 1/3664;
(Continued)

(56) References Cited

U.S. PATENT DOCUMENTS 5,385,540 A    1/1995 Abbott et al.
5,645,531 A    7/1997 Thompson et al.
(Continued)

FOREIGN PATENT DOCUMENTS

RU    2 570 391    12/2015
WO    WO 2017/055796 A1    4/2017

OTHER PUBLICATIONS

United Kingdom Intellectual Property Office, Search Report under Section 17(5)—Application No. GB1516395.9, 4 pages (dated Mar. 3, 2016).
(Continued)

*Primary Examiner* — Kai H Weng
(74) *Attorney, Agent, or Firm* — Sunstein LLP

(57) ABSTRACT

A control system controlling the blood flow rate in a blood supply system (1) in which a pump (18) transports blood from a reservoir (10) toward multiple outlets (30, 26, 26*a*) of which one or more outlets are openable to permit flow and closable to block flow, wherein the control system comprises a monitoring arrangement (22, 32, 32*a*) to determine the flow rate through a first outlet (30), and a controller responsive to the monitoring arrangement and controlling the pump (18) to maintain the flow rate through the first outlet (30) at
(Continued)

a pre-determined level. This allows a flow rate through the first outlet to be maintained independently of any active blood diversions.

18 Claims, 4 Drawing Sheets

(51) Int. Cl.
  *A61M 60/50* (2021.01)
  *A61M 60/113* (2021.01)
(52) U.S. Cl.
  CPC ........ *A61M 1/3666* (2013.01); *A61M 60/113* (2021.01); *A61M 60/50* (2021.01); *A61M 2205/3334* (2013.01); *A61M 2205/3569* (2013.01); *A61M 2205/50* (2013.01); *A61M 2210/0693* (2013.01)
(58) Field of Classification Search
  CPC ........ A61M 1/3666; A61M 2205/3334; A61M 2205/3569; A61M 2205/50; A61M 2210/0693
  See application file for complete search history.

(56) References Cited

U.S. PATENT DOCUMENTS

| | | | |
|---|---|---|---|
| 5,957,137 A | 9/1999 | Dalke et al. | |
| 2002/0150476 A1* | 10/2002 | Lucke | A61M 1/32 417/2 |
| 2005/0084416 A1 | 4/2005 | Thomas | |
| 2005/0222535 A1* | 10/2005 | Uesugi | A61B 1/042 604/26 |
| 2009/0099498 A1* | 4/2009 | Demers | A61M 1/106 604/6.09 |
| 2014/0099235 A1 | 4/2014 | Ellingboe et al. | |
| 2014/0271356 A1 | 9/2014 | Samolyk | |

OTHER PUBLICATIONS

European Patent Office, International Search Report—Application No. PCT/GB2016/052740, 19 pages (dated Mar. 9, 2017), together with the Written Opinion of the International Searching Authority.

* cited by examiner

CONTROL SYSTEM

FIELD OF THE INVENTION

The present invention relates to a blood supply control system. More specifically, the present invention relates to a control system for controlling the flow rate of blood in a blood supply system with a main blood supply channel and one or more secondary blood supply channels.

BACKGROUND

External blood circulation systems are used during surgery or external ventilation. A typical blood circulation system comprises a venous blood line in which blood from a patient is collected into a reservoir. From the reservoir, blood is pumped via a main blood line, typically through an oxygenator, and conditioned (e.g., oxygenated, pressurised, and/or brought to an appropriate temperature) for supply to a patient, and supplied to a patient in the conditioned form.

Blood from the main blood line, whether or not conditioned, may also be used for other applications, e.g., as a carrier fluid for cardioplegia, or for perfusion of specific organs (e.g., cerebral perfusion). Blood in the main line is typically pumped at a flow rate in the region of 5 litres per minute (L/min) and at a driving pressure above atmospheric pressure. The logistics of supplying the correct amounts of blood at the desired flow rate and pressure, within narrow safety margins, are challenging.

The present invention seeks to improve the blood supply management.

SUMMARY OF THE INVENTION

In accordance with a first aspect of the invention, there is provided a control system controlling the blood flow rate in a blood supply system as defined in claim 1. In the blood supply system, a first pump is provided to transport blood from a reservoir via a first passage at a flow rate toward a plurality of outlets. One or more of the outlets are openable to permit flow through the outlet and closable to block flow through the outlet. The control system comprises a monitoring arrangement to determine a flow value representative of the flow rate through a first outlet of the plurality of outlets, and a controller responsive to the monitoring arrangement, the controller configured to control the first pump to maintain the flow rate through the first outlet at a pre-determined level.

The blood supply system may be part of a perfusion system or of a heart-lung-machine, as used during surgery or extracorporeal ventilation treatment. The first passage may be constituted by the arterial-side line of the perfusion system, downstream of a blood reservoir in which venous blood from a patient is collected.

The first pump drives blood from the blood reservoir via components of the blood supply system (such as an oxygenator) towards the outlets of the system. The first pump may be understood as any arrangement that is configured to generate flow towards the outlets and that may be controlled to modulate the flow rate.

An outlet may be understood as a point at which the blood is in a condition for subsequent administration to a patient. E.g., the blood may be oxygenated, and have a pre-determined pressure, temperature, and flow rate.

Different outlets may be open to allow blood to be diverted depending on clinical demand. It may be necessary to maintain flow at a specific level through one of the outlets. The outlet through which flow is to be maintained at a specific level is the first outlet. The other outlets may be upstream and/or downstream of the first outlet. A perfusion system comprises a main arterial line for supplying blood to an outlet for subsequent supply to a patient. One or more offtakes from the main arterial line may constitute further outlets for intermittently supplying blood for cardioplegia, purging, or blood sampling. The offtakes may be regarded as secondary passages and may comprise separate pumps to draw blood from the main arterial line. In that case, the first outlet may be constituted by the main arterial line and the controller is able to maintain a pre-determined flow rate through the main arterial line independently of the number and frequency of blood diversions.

The main arterial line is not necessarily permanently open. For instance, during open heart surgery, the main blood supply to the heart may be stopped, and instead, blood may be supplied to vital organs such as the brain, and heart-beat suppressing agent may be administered to the heart. In that case, the main arterial line may be clamped and a first offtake (upstream of the clamp) may be open to supply a cerebral perfusion line and a second offtake (also upstream of the clamp) may be open to allow blood to be intermittently drawn into a cardioplegia (heart-arresting) line. In that case, the first outlet may be constituted by the cerebral perfusion line and the controller is able to maintain a pre-determined flow rate through the cerebral perfusion line independently of the amount of blood diverted into the cardioplegia line.

It will be understood that by "maintaining" a flow rate is meant that the flow rate is kept at a steady level, avoiding temporary fluctuations. The steady level is achieved by compensating the flow in proportion to fluctuations.

Modulating the first pump in dependence of the flow value, as determined by the monitoring arrangement, constitutes an interlock or feedback loop for the first outlet. The interlock operates independently of any blood diversions, i.e., independently of which outlets are open in addition to the first outlet. This allows a practically immediate adjustment to be made in order to maintain the flow rate within a pre-determined range or at a pre-determined level. This helps to avoid situations in which the amount of blood diverted would otherwise result in an unsafe flow rate through the first outlet. Unsafe conditions may include too low a flow rate, or too low driving pressure.

For instance, if a pump in a secondary passage pumps blood faster than the first pump, this may reduce the pressure in the arterial line of a perfusion system. This may cause the pressures in the blood phase to drop below the pressure in the gas phase of the oxygenator, which can lead to air being aspirated across the oxygenator into the blood phase. Air bubbles constitute an embolism hazard if delivered to a patient and need to be avoided. The risk of air aspiration through secondary-pump-induced pressure loss is reduced, and practically eliminated, by the interlock.

The controller may control the first pump to operate within a pre-determined flow range. In some embodiments, the controller may control the first pump to operate at a pre-determined flow rate or level.

By "pre-determined" it is meant that the flow rate has been determined as target flow rate for the blood to be in a condition for delivery to a patient. The pre-determined flow rate may have been set via a user interface of a control unit. The pre-determined flow rate may be obtained from the last, or latest, manually set flow rate. In this regard it may help to bear in mind that a clinician will often not set a flow rate in litres per minute (L/min) via user interface, but, instead, might adjust a flow rate "up or down" until a desired physiological response (such as a blood oxygen level) is obtained. It may not be necessary for the clinician to know the exact value of the pre-determined flow rate at which the physiological response is obtained. The flow rate thus set is regarded as pre-determined flow rate. The control system will, in that case, be able to maintain the last, or latest, set flow rate as the pre-determined flow rate (whether or not the flow value is known to the clinician).

The interlock operates on the basis of the pre-determined flow rate but independently of the level at which the pre-determined flow rate is set. Thus, if the pre-determined flow rate is set to a new range or level, the controller is responsive to maintain the (new) pre-determined flow rate whether or not blood is drawn via more than one outlet. This facilitates the setting of a new pre-determined flow rate while blood is drawn via a plurality of outlets, because it is not necessary to manually re-adjust the flow rate each time a flow diversion is open or closed. In clinical practice, the pre-determined flow rate may be set to a new level while there is no blood diversion, i.e., while blood flows only through the first outlet.

As such, the interlock increases the safety of a blood supply system.

In some embodiments, the controller is configured to receive as an input the flow value and comprises decision logic for determining a difference between the flow value and the pre-determined level and for issuing a signal to operate the first pump at pump parameters to compensate for the difference, to maintain the flow rate through the first outlet at the pre-determined level.

Maintaining the pre-determined flow rate by operating the first pump at different parameters facilitates the integration of the control system with different existing pump types. The difference between the flow value and the pre-determined level may be obtained by determining the flow of blood diverted from the primary passage.

In some embodiments, the decision logic is configured to compensate for the difference by calculating an offset value representing a change of pump parameters required to maintain the flow rate through the first outlet at the pre-determined level, and by generating the signal on the basis of the offset value.

It will be understood that an offset value is a value proportionate to the difference between the (actual) flow value and the pre-determined flow rate. Providing a control signal to the pump to alter the pump operation in proportion to the difference increases the responsiveness and the accuracy of the control system.

In some embodiments, the monitoring arrangement comprises one or more flow sensors, each flow sensor for measuring the flow rate of blood through an outlet of the plurality of outlets.

This facilitates the interlock functionality regardless of the manner in which blood is diverted towards different outlets. For instance, in a clinical setting, different tubing diameters, valves and/or pumps, from various manufacturers, may be used for various components of a blood supply system. By monitoring the actual flow rate through the first outlet, the configuration of the blood diversions need not be known in detail.

Flow information from flow sensors provided at the one or more outlets may be used to improve the accuracy of the interlock.

In some embodiments, the monitoring arrangement is configured to determine the flow value representative of the flow rate through the first outlet by analysing an operational status of the first pump.

Operational parameters from the first pump may be used to calculate the expected flow through the first outlet. This calculated value may be used to improve the accuracy of the interlock. For instance, for a peristaltic pump, the pump performance parameters may include the pump speed (typically in revolutions per minute, rpm) and the volume pumped per revolution. The flow rate for a pump may be derived by calculating the volume of blood pumped per revolution per minute. Depending on the pump type employed, the flow rate may be derived from an operational parameter such as stroke capacity and frequency, tubing diameters, etc. In other words, using the operational parameters, a flow value representative of the flow rate, or the flow rate can be determined. This allows a calculated flow rate (as determined from operational parameters) to be used instead of a measured flow rate.

In some embodiments, the control system further comprises one or more outlet pumps, each outlet pump provided to transport blood through an outlet, wherein the monitoring arrangement is configured to determine an outlet flow rate by analysing an operational status of the one or more outlet pumps, and wherein the flow value is determined based on the one or more outlet flow rates.

Operational parameters from the one or more outlet pumps may be used to improve the accuracy of the interlock in the same manner as for the first pump (main pressure pump).

With knowledge of the flow diverted from the primary passage, the likely blood flow reduction through the first outlet can be estimated or calculated. As such, the monitoring arrangement may be configured to determine the flow value by assuming that the flow value is the pre-determined flow rate minus the diverted flow (sum of the diverted outlet flow rates).

Using operational parameters of the outlet pumps reduces the risk of an overshooting response, because the pump parameters can be used as an input for determining and/or adjusting the magnitude and duration of any compensation required.

Furthermore, this facilitates using a pre-determined flow rate without requiring a set flow rate as input parameter. The control system may, when the flow rate through the main arterial line is set, determine whether or not any blood diversions are active.

If there are no blood diversions active, the control system derives the pre-determined flow rate from the first outlet (e.g., the main arterial line). This may be by way of input from a control system, by measuring the flow using a flow sensor, and/or by calculating the flow from operational parameters of the first pump. The flow rate thus determined corresponds to the latest flow rate set by a clinician and is interpreted by the control system as the pre-determined flow rate.

If there are one or more blood diversions active while the flow rate through the first outlet (e.g., the main arterial line) is set, the control system derives the flow rate through the first outlet as set out above, and is also able to determine the flow through any blood diversions (by way of input from a control system, by measuring the flow using a flow sensor, and/or by calculating the flow from operational parameters of an outlet pump). The pre-determined flow rate is obtained by taking into account the effect of the cumulative outlet flow values on the flow value through the first outlet. Thus, when the blood diversions stop and blood is supplied only via the first outlet, the control system is able to compensate for the lower blood flow demand and maintain the pre-determined flow rate as if it was set during a phase without blood diversions.

This allows the pre-determined flow rate to be determined regardless of the number of active blood diversions.

Furthermore, this allows the pre-determined flow rate to be determined whether or not this is provided as a specific value from an input system or set via a separate control unit. This facilitates the integration of the control system with existing equipment.

In some embodiments, the control system is configured to calibrate components of the monitoring arrangement on the basis of one or more outlet flow rates.

The outlet flow rates may include the flow rate through the first outlet. In embodiments in which the monitoring arrangement determines a flow value representative of the flow rate, the flow value can be calibrated on the basis of the measured flow rate. For instance, if the flow value is determined on the basis of performance parameters of the first pump or of an outlet pump (e.g. rpm and predicted volume pumped per rpm), the actual performance of the pump may be calibrated by calculating measured flow per rpm. In this manner, the predicted performance of the pump can be related to the actually measured outlet flow. This allows compensating for any unaccounted losses in pump performance. This provides a more accurate indication of the amount of blood transported per pump rpm.

This also allows communication between components of the control system to be facilitated. For instance, once calibrated, an outlet pump may only need to send its rpm setting to the controller, and—based on the rpm setting—the controller can derive the amount of diverted blood, and, consequently, the flow value and any offset value with high accuracy. As another example, once calibrated, the rpm setting of the first pump may be monitored by the controller, to derive the pre-determined flow rate that would be expected through the first outlet in the absence of any blood diversions.

The interlock to maintain a pre-determined flow rate may be reactive, contemporaneous, or proactive. A flow sensor provides a direct measurement for a reactive interlock. By "reactive" is meant that the interlock requires actual flow to be measured before being able to compensate. The evaluation of pump parameters provides an indirect determination and the interlock may be contemporaneous or proactive. By "contemporaneous" is meant that controller receives the outlet pump parameters as an input from the outlet pump or from a controller of the outlet pump, such as a user interface, as they are signalled to the outlet pump, and modulates the primary pump in response. By "proactive" is meant that the controller issues control signals to the primary pump to maintain a pre-determined flow rate.

By calibrating the outlet pumps, accuracy levels similar or equal to a direct measurement can be ensured while providing a contemporaneous or pro-active interlock.

In some embodiments, the controller is configured to determine that an outlet is open depending on the operational status of a corresponding outlet pump.

In some embodiments, the controller is configured to determine that an outlet is open when the outlet flow rate exceeds a pre-determined threshold.

This allows the interlock to be activated only if a pre-determined threshold value is exceeded. This may help to avoid overshooting responses of the controller.

In some embodiments, the monitoring arrangement is further configured to determine a line pressure in the first passage, and the controller is configured to prevent operation of one or more outlet pumps if the line pressure is below a pre-set threshold level.

One or more pressure sensors may be provided as part of the monitoring arrangement. The pressure sensors may measure the line pressure in the primary passage.

The control system may be provided with a minimum driving pressure. In the field, pressures are conventionally provided in mmHg relative to atmospheric pressure (1 atm corresponds to 101.325 kPa, or 760 mmHg). A blood pressure of 100 mmHg (above atmospheric pressure) would correspond to a total pressure of 860 mmHg. Although the minimum driving pressure may depend on various factors, such as patient position and posture, a typical driving pressure in a main line of a perfusion system is in a region of 200 to 300 mmHg (26.7 to 40.0 kPa), as opposed to the mean coronary pressures in the region of 20 to 120 mmHg (2.67 to 16.0 kPa).

The pre-set threshold level may be a pressure level above atmospheric pressure. A line pressure above atmospheric pressure indicates that the first pump is operating (regardless of the flow rate, which may be low). The pre-set threshold level may be e.g., at 10 mmHg, 20 mmHg, 30 mmHg or 50 mmHg.

If the line pressure is below the pre-set threshold level, this may be interpreted as an indication that the first pump is not pumping and actuation of an outlet pump risks creating a negative pressure gradient in the main line. By providing a mechanism that prevents operation of an outlet pump while the line pressure is too low (i.e., below the pre-set threshold level), it can be ensured that outlet pumps only activate if there is flow in the main line.

In some embodiments, at least one outlet is configured to provide blood suitable for use in a cerebral perfusion line.

In some embodiments, at least one outlet is configured to provide blood suitable for use in a cardioplegia line.

In some embodiments, at least one outlet is configured to provide blood suitable for use in a purge line.

This may include any purge line, including, e.g., as a source of blood to be run through an ultrafiltration system.

In some embodiments, at least one outlet is configured to provide blood suitable for use in a blood sampling offtake.

In some embodiments, one or more of the first pump, the one or more flow sensors, the one or more outlet pumps, one or more pressure sensors, the controller, and/or the monitoring arrangement are configured to exchange data via a network connection.

This improves the reliability of the data transfer. With a reliable data connection, monitoring and control steps can be carried out with higher frequency.

Furthermore, this facilitates the transfer of settings. For instance, as part of the monitoring arrangement, the pump parameters may be determined for each pump and transmitted to the controller. As another option, the pump parameters may be set at an interface and may be transmitted as instructions to each pump and to the monitoring arrangement as input values for determining the flow value. This improves the options of providing a reactive, contemporaneous, and/or proactive interlock.

In some embodiments, the controller comprises a processor and software instructions implemented by the processor.

In accordance with a second aspect of the invention, there is provided a method of controlling the blood flow rate in a blood supply system as defined in claim 17. In the blood supply system, a first pump is provided to transport blood from a reservoir via a first passage at a flow rate toward a plurality of outlets of which one or more outlets are openable to permit flow through the outlet and closable to block flow through the outlet. The method comprises the steps of determining a flow value representative of the flow rate through a first outlet of the plurality of outlets, and controlling the first pump to maintain the flow rate through the first outlet at a pre-determined level.

In some embodiments, the method comprises determining a difference between the flow value through the first outlet and the pre-determined level, and issuing a signal to operate the first pump at pump parameters to compensate for the difference, to maintain the flow rate through the first outlet at the pre-determined level.

In some embodiments, the method comprises calculating an offset value representing a change of pump parameters required to maintain the flow rate through the first outlet at the pre-determined level, and generating the signal on the basis of the offset value.

In some embodiments, the method comprises providing one or more flow sensors, and using each flow sensor to measure the flow rate of blood through an outlet of the plurality of outlets.

In some embodiments, the method comprises analysing an operational status of the first pump, and determining the flow value representative of the flow rate through the first outlet by analysing an operational status of the first pump.

In some embodiments, the method comprises providing one or more outlet pumps, each outlet pump to draw blood through an outlet, analysing an operational status of the one or more outlet pumps, determining one or more outlet flow rates based on the operational status, and determining the flow value based on the one or more outlet flow rates.

In some embodiments, the method comprises calibrating a component of the monitoring arrangement on the basis of the one or more outlet flow rates.

In some embodiments, the method comprises determining that an outlet is open depending on the operational status of a corresponding pump.

In some embodiments, the method comprises determining that an outlet is open when the outlet flow rate exceeds a pre-determined threshold.

In some embodiments, the method comprises determining a line pressure in the first passage, and preventing operation of one or more outlet pumps if the line pressure is below a pre-set threshold level.

In some embodiments, the method comprises providing through at least one outlet blood suitable for use in a cerebral perfusion line.

In some embodiments, the method comprises providing through at least one outlet blood suitable for use in a cardioplegia line.

In some embodiments, the method comprises providing through at least one outlet blood suitable for use in a purge line.

This may include any purge line, including, e.g., as a source of blood to be run through an ultrafiltration system.

In some embodiments, the method comprises providing through at least one outlet blood suitable for use in a blood sampling offtake.

In some embodiments, the method comprises providing a network connection to exchange data between one or more of the first pump, the one or more flow sensors, the one or more outlet pumps, one or more pressure sensors, the controller, and/or the monitoring arrangement.

In accordance with a third aspect of the invention, there is provided a calibration method to calibrate a feedback loop of a blood supply system as defined in claim 32. In the blood supply system, a pump is provided to transport blood at a flow rate from a reservoir via a passage through a plurality of outlets of which one or more outlets are openable to permit flow through the outlet and closable to block flow through the outlet. The method comprises the steps of specifying a first pump parameter setting, determining an outlet configuration indicative of which outlets are open, operating the pump with the first pump parameter setting, determining the flow rate through each open outlet, and calculating a calibration value for the outlet configuration by relating the flow rate to the first pump parameter setting.

The calibration value may be employed to calibrate the operational parameters of the first pump, to improve the accuracy of the feedback loop in embodiments of the first aspect and the second aspect of the invention. This improves the accuracy of flow values calculated from the operational parameters of a pump. For instance, the flow generated by a peristaltic pump may be determined from the number of revolutions if the volume of blood pumped per revolution is known. For a given pump setup, the number of revolutions may be the only variable required to determine flow, the other variables (e.g., volume per revolution or per stroke, tubing dimensions etc.) being constant. Calibrating the pump increases the accuracy of the parameters obtained from the pump.

In some embodiments, the calibration method further comprises the steps of altering the outlet configuration to provide an altered outlet configuration, determining the altered outlet configuration, and calculating a calibration value for the altered outlet configuration by relating the flow rate to the first pump parameter setting.

This improves the accuracy of the calibration values for different outlet configurations.

In accordance with a fourth aspect of the invention, there is provided a calibration method to calibrate a feedback loop of a blood supply system as defined in claim 34. In the blood supply system a first pump is provided to transport blood from a reservoir at a first flow rate via a first passage through a first outlet. A diverting pump is provided to draw blood from the first passage into a secondary passage. The method comprises the steps of specifying a first pump parameter setting for the diverting pump, operating the first pump at the first flow rate, operating the diverting pump with the first pump parameter setting, measuring the diverted flow rate in the secondary passage while the diverting pump is operated with the first parameter setting, and calculating a calibration value for the diverting pump by relating the diverted flow rate to the first pump parameter setting.

A secondary passage is a passage through a diverting outlet. The diverting pump may be an outlet pump, such as a pump for drawing blood from a main arterial line constituting a primary passage into a cardioplegia line constituting a secondary passage.

The operational parameters of the diverting pump may be used in embodiments of the first aspect and the second aspect of the invention as part of a monitoring arrangement. This improves that accuracy of flow values calculated from operational parameters of a diverting pump, as described above in relation to the first pump or the outlet pumps.

DESCRIPTION OF THE FIGURES

Exemplary embodiments of the invention will now be described with reference to the Figures, in which.

DESCRIPTION

Figure 1:
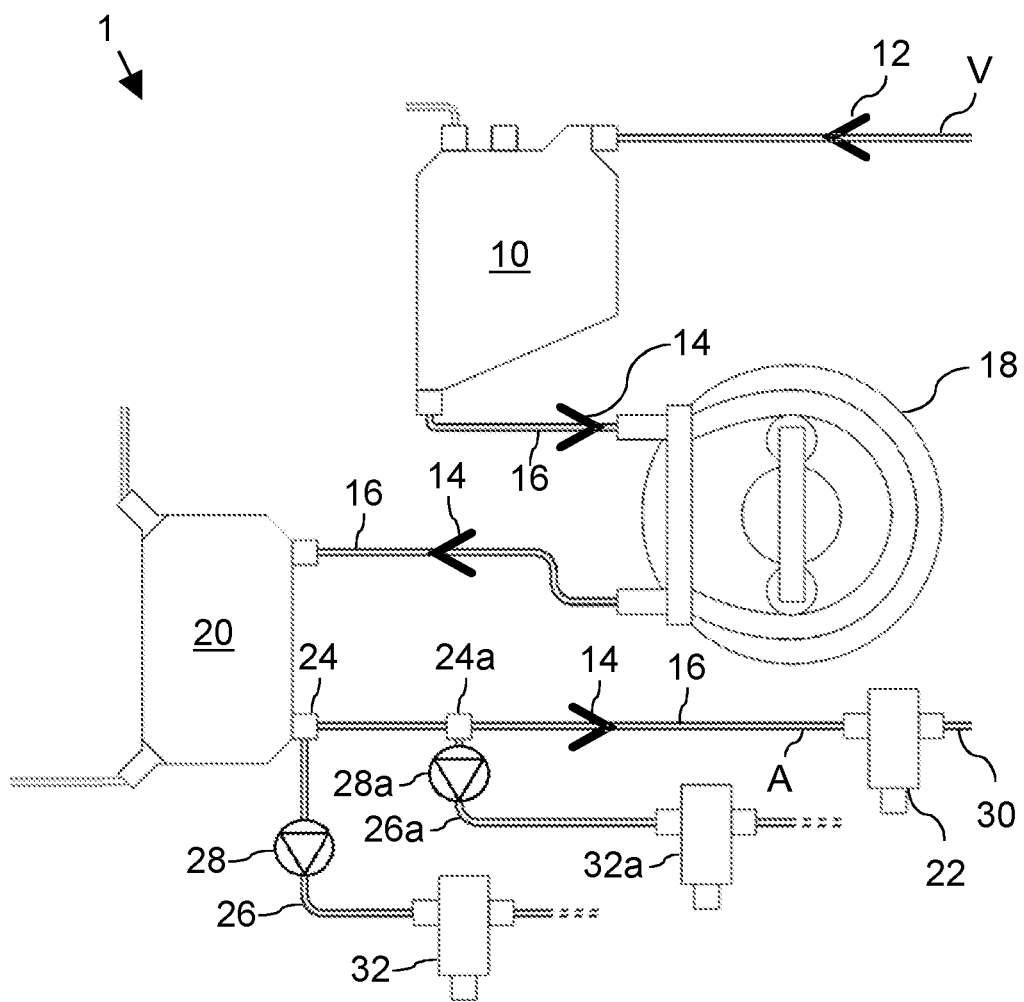
FIG. 1 shows a schematic arrangement of a blood supply control system in accordance with an exemplary embodiment of the present invention.

FIG. 1 shows a perfusion system 1 constituting part of a blood supply system, comprising a venous blood line V supplying blood in a direction 12 into a venous blood reservoir 10. A peristaltic pump 18 constitutes a first pump and is provided as a system pressure pump to transport blood from the venous reservoir 10 along the tubing 16 in direction 14 via an oxygenator 20 towards and through an arterial outlet 30. The tubing 16 constitutes a first passage from the venous blood reservoir 10 to the arterial outlet 30. The arterial outlet 30 may constitute a first outlet. It is understood that the arterial outlet 30 is not necessarily constituted by an orifice or end connection of the tubing 16. The arterial outlet 30 may be understood as a point at which the blood is conditioned for subsequent delivery to a patient. Downstream of the oxygenator 20, the blood is oxygenated, and the oxygenated blood line may be referred to as an arterial line A. The blood may be conditioned in other respects, such as having a specific driving pressure, flow rate, and temperature.

Downstream of the oxygenator 20 and upstream of the first outlet 30, the tubing 16 comprises a first Y-junction 24 into a second tubing 26. The second tubing 26 constitutes another outlet and comprises an outlet pump 28 which permits a portion of the blood to be drawn from the main blood supply, i.e., from the arterial line A, upstream of the first outlet.

Downstream of the first Y-junction 24, a second Y-junction 24a is located in the tubing 16, leading into a third tubing 26a. The third tubing 26a constitutes another outlet and comprises, similar to the second tubing 26, another outlet pump 28a. The second tubing 26 and the third tubing 26a constitute a plurality of outlets, each permitting a portion of blood to be drawn, via their respective Y-junctions 24 and 24a, from the arterial line A, upstream of the first outlet.

The different outlets permit blood to be drawn for, e.g., use as a carrier fluid for cardioplegic (heart-arresting) agent, or as source of oxygenated blood for cerebral or other organ perfusion. The blood may be drawn from the arterial line A intermittently, as and when needed. Regardless of the underlying purpose and frequency, blood diverted from the arterial line A reduces the amount of blood flow at the first outlet.

A first flow sensor 22 is provided in the first passage (in FIG. 1, near the first outlet 30). Likewise, a second flow sensor 32 is provided in the second tubing 26 and a third flow sensor 32a is provided in the third tubing 26a. The first flow sensor 22 is part of a monitoring arrangement and allows a flow value to be determined that is representative of the flow rate through the first outlet 30. In some embodiments, the second flow sensor 32 and/or the third flow sensor 32a are part of the monitoring arrangement. In some embodiments, one or both of the outlet pumps 28 and 28a are part of the monitoring arrangement.

The flow value is provided as an input to a controller (not shown in FIG. 1), which is configured to determine whether the flow rate at the arterial outlet 30 is equal to a pre-determined level. If the flow rate is not equal to the pre-determined level, the controller may issue a signal to the peristaltic pump 18 to alter the flow rate, in order to maintain the flow rate equal to the pre-determined level.

The first outlet may be constituted by the second tubing 26. For instance, during open heart surgery, the arterial outlet 30 may be clamped and the second tubing 26 may be opened to supply a cerebral perfusion line. Further, the third tubing 26a may be used to intermittently supply blood as a carrier fluid for a cardioplegia line. In that case, the flow value may be determined for the second tubing 26, for instance from the second flow sensor 32, or from performance parameters of the outlet pump 28, in order to maintain a pre-determined flow rate through the cerebral perfusion line. Thus, although flow sensors 22, 32 and 32a are shown in FIG. 1, the control system may not need to use flow sensors and derive or calculate flow rates from operational parameters of the pumps.

Figure 2:
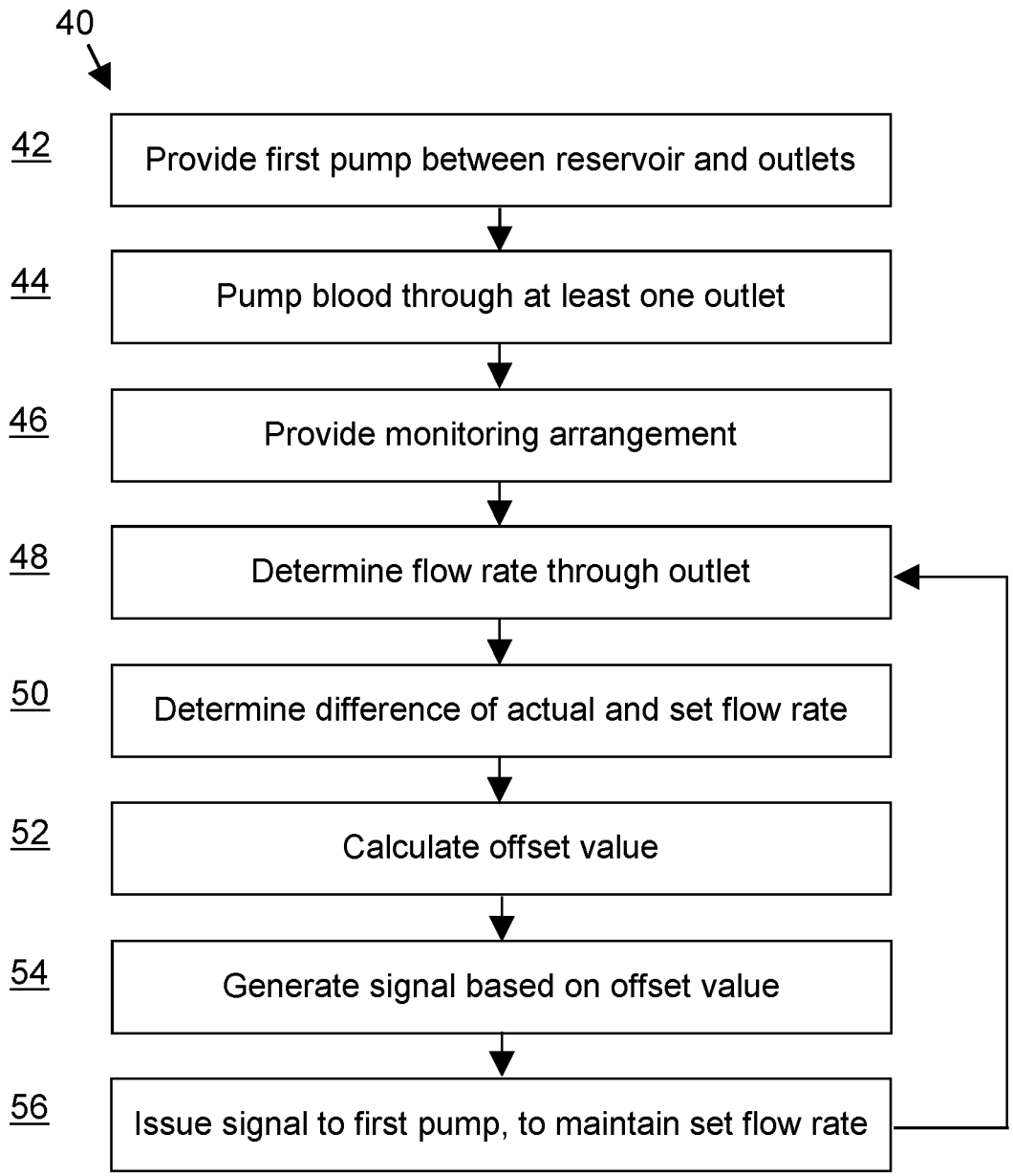
FIG. 2 shows an exemplary sequence of steps of a blood supply control method in accordance with an exemplary embodiment of the present invention.

FIG. 2 sets out steps of an exemplary method 40 for controlling the blood flow rate in a blood supply system. In step 42, a first pump is provided to transport blood in a first passage from a blood reservoir towards a plurality of outlets at a flow rate. In step 44, blood is pumped through one or more outlets. It will be understood that any number of outlets may be open. One of the outlets is considered a first outlet through which a pre-determined flow rate is to be maintained. In step 46, a monitoring arrangement is provided to determine a flow value representative of the flow rate through the first outlet. This may be provided in the form of one or more flow meters at the first outlet and/or any of the other outlets. The arrangement may calculate the values from pump parameters of one or more pumps (first pump and/or any outlet pumps). In step 48, the monitoring arrangement determines the flow rate through the first outlet. This may be achieved by measuring the flow rate downstream of any blood diversions. As an alternative or in addition, the flow rate may be determined by calculating the amount of blood diverted through outlets other than the first outlet. In step 50, a controller determines whether or not there is a difference between the flow rate as measured and the pre-determined flow rate. In step 52, an offset value is calculated. The offset value may be proportional to the difference between the measured or calculated flow value and the pre-determined flow rate. The offset value may be proportional to the diverted blood flow as determined by flow meters and/or as determined from operational parameters of the one or more outlet pumps. In step 54, the controller generates, on the basis of the offset value, a signal to change the pump parameters of the first pump in order to compensate for any difference in flow rate. In step 56, the signal is issued to the pump, in order to maintain the pre-determined flow rate through the first outlet. Steps 48 to 56 are repeated in order to continue with the monitoring of the flow rate.

To illustrate this with exemplary values, the pre-determined flow rate in the first passage through the first outlet may be in the region of 4-6 litres per minute (L/min), at a flow rate set by a clinician. In the absence of any losses, the first pump operates at the set flow rate. The control system determines from the rpm setting of the first pump that the set flow rate is 5 L/min and interprets this as the pre-determined flow rate. In other words, the control system derives that the flow rate through the first outlet should, in the absence of any blood diversions, be 5 L/min. The control system will maintain the pre-determined flow rate regardless of any blood diversions. One of the other outlets may be a cardioplegia line. When cardioplegic agent is to be administered, a cardioplegia line pump in the cardioplegia line may draw 300 millilitres of blood per minute from the first passage as carrier fluid for cardioplegic agent. Thereby, the flow rate at the first outlet is reduced from 5 L/min by 300 mL/min to 4.7 L/min. The monitoring arrangement determines the flow value as 4.7 L/min and relays this value to the controller. The flow value may be determined by direct measurement at the first outlet, measuring a flow of 4.7 L/min. The flow value may be determined by direct measurement at the cardioplegia outlet, measuring a diverted flow of 0.3 L/min, whereby the flow value can be derived (5 L/min pre-determined flow−0.3 L/min diverted flow=4.7 L/min flow value). The flow value may be determined by analysing the operational parameters of the cardioplegia line pump, indicating a diverted flow of 0.3 L/min. The controller determines the difference between the flow value and the pre-determined flow rate (4.7 L/min−5 L/min=−0.3 L/min). If there are multiple blood diversions, the controller may determine that the difference is equal to the sum of all diverted flows. The controller generates a control signal to alter the pump parameters (e.g., pump speed, or pump volume) of the first pump to compensate for the change in flow rate. The parameters of the first pump are altered (e.g., by setting the pump speed to an increased level), in response to a control signal, in order to maintain a flow rate of 5 L/min through the first outlet.

It will be understood that the flow rate is monitored continuously, e.g., in intervals of 1 second. Thus, when the cardioplegia line no longer draws blood, this is registered by the monitoring arrangement, and the controller generates a control signal to compensate for the change in flow rate (e.g., by setting the pump speed to a reduced level), to maintain the pre-determined flow rate of 5 L/min through the first outlet.

If, in the example, the pre-determined flow rate has to be adjusted to 5.5 L/min, this can be set and maintained without having to consider blood diversion into the cardioplegia line. The pre-determined flow rate can be adjusted to the new level while the cardioplegia pump is drawing blood from the first passage. For instance, the control system will interpret the change in pump speed of the first pump and derive the new pre-determined flow rate (compensating for the currently active cardioplegia pump). Once the cardioplegia pump stops, the controller will compensate for the reduced blood demand and maintain the new flow rate of 5.5 L/min.

The controller is, likewise, able to maintain the pre-determined flow rate if blood is drawn via another outlet, by adjusting the pump parameters in the manner explained above. By providing a flow sensor, the flow rate through the first outlet can be monitored and maintained independently of the number and frequency of blood diversions from the first passage.

If one of the outlet pumps 28 or 28a is part of the monitoring arrangement, an operational parameter of the secondary pumps 28 or 28a may be provided as an input to the controller, to indicate that blood is diverted. This data may be used as an alternative to a direct flow measurement, and/or in a complementary manner, to improve the accuracy of the offset value.

The control of the first pump in relation to values determined by the monitoring arrangement constitutes an interlock that ensures that the blood flow rate at the first outlet is maintained at the pre-determined level regardless of the number of active blood diversions and regardless of any amount of blood diverted.

The controller (not shown in FIG. 1) may be a separate component. The controller may be integrated with one of the pumps, e.g., the first pump 18. There may be a direct data connection between the components of the monitoring arrangement and the first pump 18. For instance, there may be a data connection between the first flow sensor 22, the second flow sensor 32, or the third flow sensor 32a, and the first pump 18. There may be a data connection between the secondary pumps 28 or 28a and the first pump 18.

Although diversions are indicated in FIG. 1 in the form of two Y-junctions 24 and 24a, diversions may be connected to any point in the first passage, and they may include Y-junctions, stop cocks, or other suitable components. For instance, blood may be drawn directly from a port of the oxygenator 20. Blood may be diverted upstream the oxygenator 20.

Two outlets (second tubing 26 and third tubing 26a) are shown in the embodiment of FIG. 1. It will be understood that any number of blood-diverting components can be installed as part of the blood supply system. A flow-monitoring arrangement that permits the flow rate at the first outlet to be determined facilitates the blood supply management to a large number of secondary devices, because the interlock with the first pump ensures that the flow rate of conditioned blood to the first outlet is maintained at the pre-determined level. In the specific examples, the controller operates the pump to maintain a flow rate at the pre-determined level. In some embodiments, the controller may operate the pump to maintain the flow rate within a pre-determined range. In some embodiments, the pre-determined level may be within the pre-determined range, and the boundaries of the range may constitute an activation threshold before the flow rate is compensated. This may reduce the risk of an overshooting and/or hunting (oscillating) response.

The specific example includes a peristaltic pump (roller pump) 18. Other pump types may be used. In some embodiments, the first pump is constituted by a centrifugal pump. The provision of a flow sensor allows an interlock to be provided regardless of the type of pump.

Figure 3:
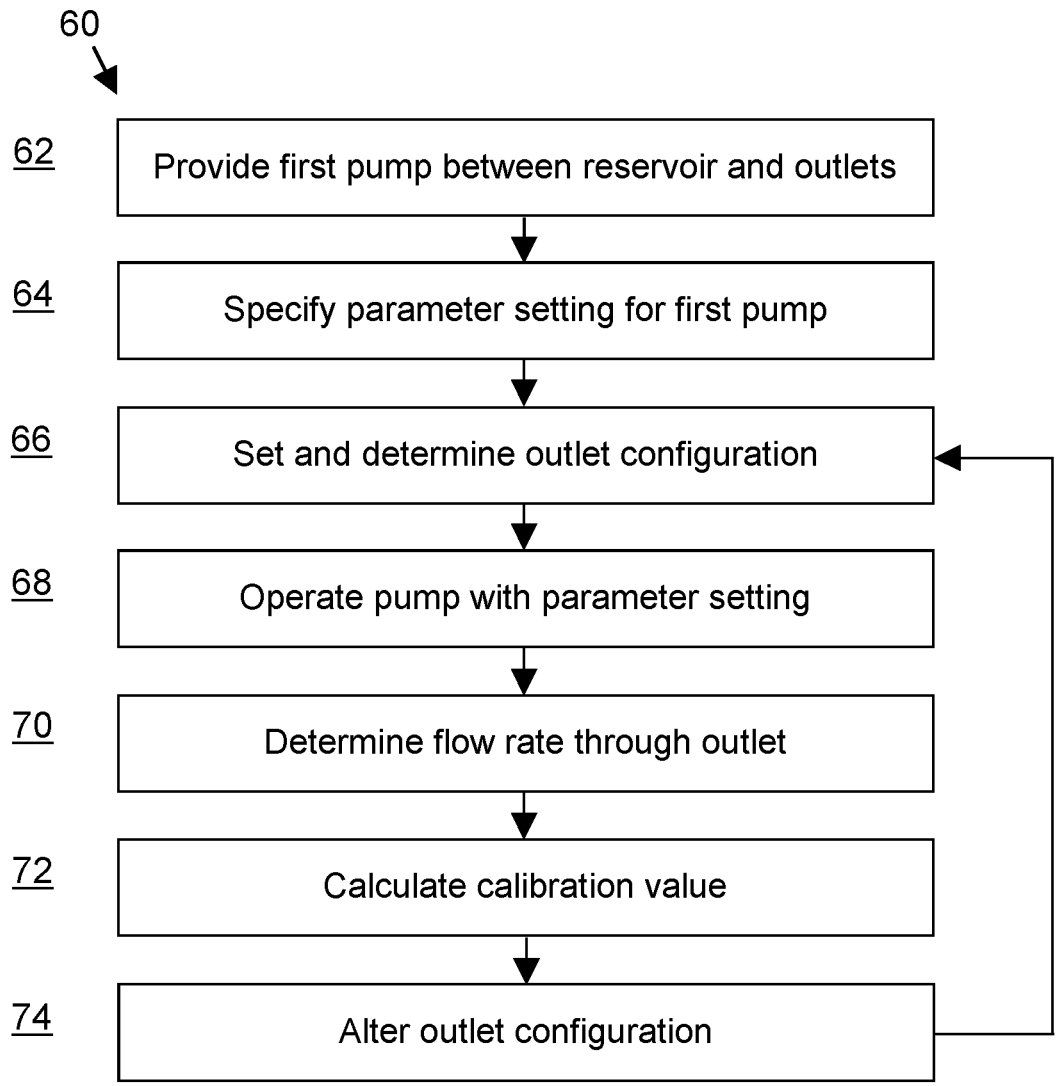
FIG. 3 shows an exemplary sequence of steps of a calibration method in accordance with an exemplary embodiment of the present invention.

FIG. 3 shows steps of an exemplary calibration method 60 for calibrating a pump in a blood supply system. In step 62, a first pump is provided to transport blood in a first passage from a blood reservoir toward a first outlet, or toward one or more outlets. In step 64, pump parameters are specified for the first pump. For instance, the pump may be set to pump blood at a set rpm value corresponding to an expected flow rate of 5 L/min. In step 66, an outlet configuration is determined. For instance, only one outlet of the plurality of outlets may be open, e.g., only the main arterial line may be open, without any diversions being active. The outlet configuration can be regarded as a register of open outlets. In step 68, the pump is operated with the pump parameters. E.g., the pump may be operated to pump at the set rpm value. In step 70, the actual flow rate through the open outlets is measured with a flow meter. For instance, the flow meter may measure an actual flow rate of 4.90 L/min that is lower than the set rate, due to pump inefficiencies. In step 72, a calibration value is calculated. For instance, a calibration value $rpm_{EFFECTIVE} = rpm_{SET} \times flow_{SET} / flow_{MEASURED}$, wherein $rpm_{SET}$ is the set rpm value, $flow_{SET}$ is the flow rate expected to correspond to the set rpm value, and flow$_{MEASURED}$ is the actual flow rate as measured by the flow sensor. After step 72, the method may be repeated with new pump parameters different from the previous pump parameters. In optional step 74, the outlet configuration is altered. For instance, a different outlet may be opened, and a new calibration value is calculated for the new outlet configuration.

The parameter setting may differ for different outlet configurations. Thus, a calibration value may be obtained for different system configurations.

Figure 4:
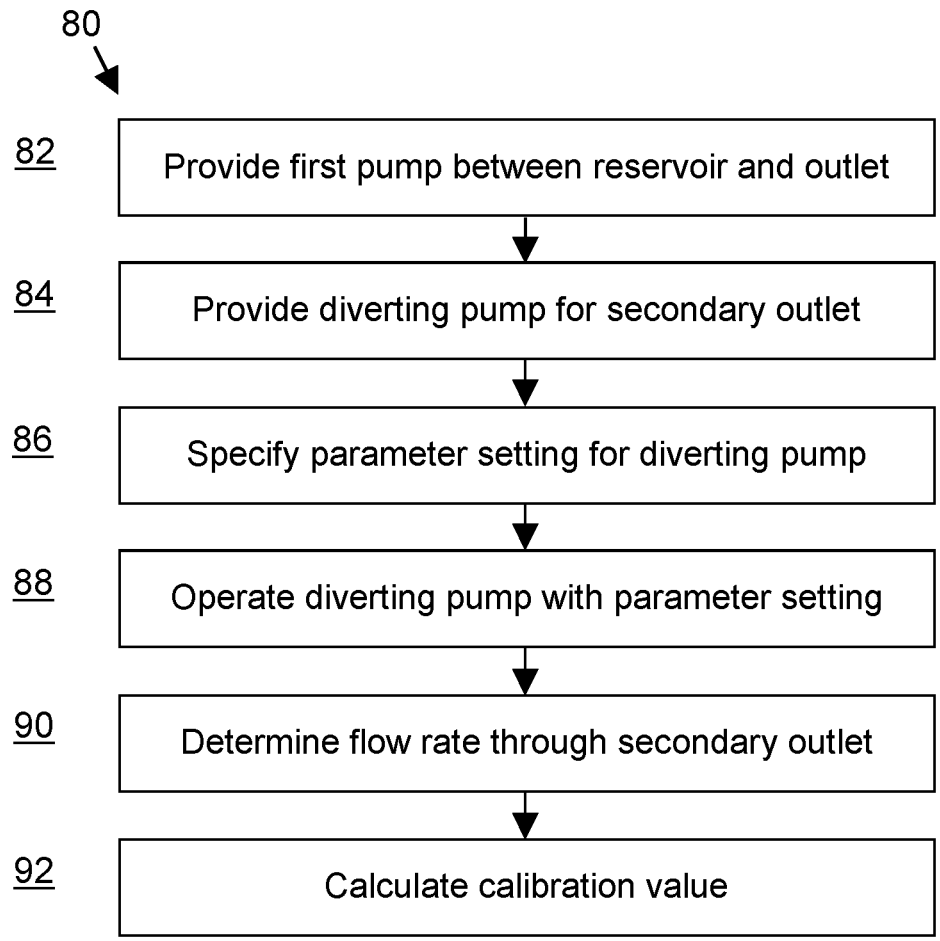
FIG. 4 shows an exemplary sequence of steps of a calibration method in accordance with another exemplary embodiment of the present invention.

FIG. 4 shows steps of an exemplary calibration method 80 for calibrating a pump in a blood supply system. In step 82, a first pump is provided to transport blood in a first passage from a blood reservoir toward a first outlet, or toward one or more outlets. In step 84, a diverting pump is provided to divert blood from the first passage into a secondary passage. In step 86, pump parameters are specified for the diverting pump. For instance, the pump may be set to pump blood at a set rpm value corresponding to an expected flow rate of 0.5 L/min. In step 88, the diverting pump is operated with the pump parameters. E.g., the pump may be operated to pump at the set rpm value. In step 90, the actual flow rate through the first outlet is measured with a flow meter. For instance, the flow meter may measure an actual flow rate of 0.45 L/min that is lower than the set rate, due to pump inefficiencies. In step 92, a calibration value is calculated. For instance, a calibration value rpm$_{EFFECTIVE}$=rpm$_{SET}$×flow$_{SET}$/flow$_{MEASURED}$, wherein rpm$_{SET}$ is the set rpm value, flow$_{SET}$ is the flow rate expected to correspond to the set rpm value, and flow$_{MEASURED}$ is the actual flow rate as measured by the flow sensor.

The calibration values thus determined allow the feedback loop to be operated with higher accuracy.

The invention claimed is:

1. A control system for controlling the blood flow rate in a blood supply system in which a first pump is provided to transport blood from a reservoir via a first passage at a flow rate toward a plurality of outlets of which one or more of the outlets are openable to permit flow through the outlet and closable to block flow through the outlet, wherein the plurality of outlets includes a first outlet and one or more further outlets,
wherein the control system comprises:
a monitoring arrangement to determine a flow value representative of the flow rate through the first outlet of the plurality of outlets,
one or more outlet pumps, each outlet pump provided to transport blood through a corresponding one of the further outlets, and
a controller responsive to the monitoring arrangement,
wherein the monitoring arrangement is configured to determine outlet flow rates of the one or more further outlets from outlet pump parameters of the corresponding outlet pumps or by analyzing an operational status of the corresponding outlet pumps,
wherein the flow value is determined based on the one or more outlet flow rates, and
wherein the controller is configured to contemporaneously or proactively control the first pump to maintain the flow rate through the first outlet at a pre-determined level.

2. The control system according to claim 1, wherein the monitoring arrangement is configured to determine the flow value representative of the flow rate through the first outlet by analyzing an operational status of the first pump.

3. The control system according to claim 1, configured to calibrate components of the monitoring arrangement on the basis of one or more outlet flow rates.

4. The control system according to claim 1, wherein the controller is configured to determine that an outlet is open depending on the operational status of a corresponding outlet pump.

5. The control system according to claim 1, wherein the controller is configured to determine that an outlet is open when the outlet flow rate exceeds a pre-determined threshold.

6. The control system according to claim 1, wherein the monitoring arrangement is further configured to determine a line pressure in the first passage, and wherein the controller is configured to prevent operation of one or more outlet pumps if the line pressure is below a pre-set threshold level.

7. The control system according to claim 1, wherein at least one outlet is configured to provide blood suitable for use in at least one selected from the group consisting of a cerebral perfusion line, a cardioplegia line, a purge line, and a blood sampling offtake.

8. The control system according to claim 1, wherein at least one selected from the group consisting of one or more of the first pumps, the one or more flow sensors, the one or more outlet pumps, the one or more pressure sensors, the controller, and the monitoring arrangement is configured to exchange data via a network connection.

9. A control system according to claim 1, wherein the controller comprises a processor and software instructions implemented by the processor.

10. A method of controlling the blood flow rate in a blood supply system in which a first pump is provided to transport blood from a reservoir via a first passage at a flow rate toward a plurality of outlets of which one or more of the outlets are openable to permit flow through the outlet and closable to block flow through the outlet, the plurality of outlets including a first outlet and one or more further outlets, the blood supply system further comprising one or more outlet pumps to transport blood through a corresponding one of the further outlets, the method comprising:
determining a flow value representative of the flow rate through the first outlet of the plurality of outlets,
determining outlet flow rates of the one or more further outlets from outlet pump parameters of the corresponding outlet pumps, or by analyzing an operational status of the corresponding outlet pumps, wherein the flow value is determined based on the one or more outlet flow rates, and
controlling the first pump, contemporaneously or proactively, to maintain the flow rate through the first outlet at a pre-determined level.

11. The method according to claim 10, further comprising:
analyzing an operational status of the first pump, and
determining the flow value representative of the flow rate through the first outlet by analyzing an operational status of the first pump.

12. The method according to claim 10, further comprising:
determining that an outlet is open depending on the operational status of a corresponding outlet pump.

13. The method according to claim 10, further comprising:
determining that an outlet is open when the outlet flow rate exceeds a pre-determined threshold.

14. The method according to claim 10, further comprising determining a line pressure in the first passage, and preventing operation of one or more outlet pumps if the line pressure is below a pre-set threshold level.

15. The method according to claim 10, further comprising:
providing a network connection to exchange data between at least one selected from a group consisting of one or more of the first pump, the one or more flow sensors, the one or more outlet pumps, one or more pressure sensors, the controller, and the monitoring arrangement.

16. The method according to claim 10, further comprising:
specifying a first pump parameter setting,
determining an outlet configuration indicative of which outlets are open,
operating the first pump with the first pump parameter setting,
determining the flow rate through each open outlet, and
calculating a calibration value for the outlet configuration by relating the flow rate to the first pump parameter setting.

17. The method according to claim 16, further comprising:
altering the outlet configuration to provide an altered outlet configuration,
determining the altered outlet configuration, and
calculating a calibration value for the altered outlet configuration by relating the flow rate to the first pump parameter setting.

18. The method according to claim 10, wherein a diverting pump is provided to draw blood from the first passage into a secondary passage, the method comprising:
specifying a first pump parameter setting for the diverting pump,
operating the diverting pump with the first pump parameter setting,
measuring the diverted flow rate in the secondary passage while the diverting pump is operated with the first pump parameter setting, and
calculating a calibration value for the diverting pump by relating the diverted flow rate to the first pump parameter setting.

* * * * *